United States Patent
Quinones

(10) Patent No.: US 11,648,363 B2
(45) Date of Patent: May 16, 2023

(54) POSITIVE PRESSURE VENTILATION APPARATUS AND POSITIVE PRESSURE MASK

(71) Applicant: Alphonso Quinones, East Meadow, NY (US)

(72) Inventor: Alphonso Quinones, East Meadow, NY (US)

( * ) Notice: Subject to any disclaimer, the term of this patent is extended or adjusted under 35 U.S.C. 154(b) by 0 days.

(21) Appl. No.: 17/678,771

(22) Filed: Feb. 23, 2022

(65) Prior Publication Data

US 2022/0226593 A1 Jul. 21, 2022

Related U.S. Application Data

(63) Continuation-in-part of application No. 16/839,014, filed on Apr. 2, 2020, now abandoned.

(51) Int. Cl.
*A61M 16/06* (2006.01)

(52) U.S. Cl.
CPC .... *A61M 16/0611* (2014.02); *A61M 16/0683* (2013.01)

(58) Field of Classification Search
CPC ................ A61M 16/0611; A61M 16/0688
See application file for complete search history.

(56) References Cited

U.S. PATENT DOCUMENTS

| | | | |
|---|---|---|---|
| 5,590,644 A * | 1/1997 | Rosenkoetter .... | A61M 16/1045 128/205.12 |
| 5,918,598 A * | 7/1999 | Belfer ................ | A41D 13/1192 128/206.25 |
| 6,196,223 B1 * | 3/2001 | Belter ................ | A61M 16/0616 128/206.25 |
| 8,381,727 B2 * | 2/2013 | Matich ............... | A41D 13/1169 128/206.25 |
| 2002/0029780 A1 * | 3/2002 | Frater ................ | A61M 16/0633 128/206.27 |
| 2002/0185134 A1 * | 12/2002 | Bishop .............. | A61M 16/0688 128/206.25 |
| 2005/0098183 A1 * | 5/2005 | Nash ................. | A61M 16/0683 128/206.27 |

(Continued)

*Primary Examiner* — Joseph D. Boecker
*Assistant Examiner* — Thomas W Greig
(74) *Attorney, Agent, or Firm* — Brooklyn Law Incubator and Policy Clinic; Serge Krimnus; Jacqueline Zahn

(57) ABSTRACT

A positive pressure ventilation apparatus may include a positive pressure mask; a positive pressure source; and an exhalation filter. The positive pressure mask may include a mask body having a patient-contact perimeter and including a flexible concertinaed portion of uniform flexion continuously around the mask body. The flexible concertinaed portion may include a plurality of ridges. The positive pressure mask may further include a gas inlet to the mask body configured to be connected to the positive-pressure source; and an adhesive seal positioned at the patient-contact perimeter which may be positioned at the outermost portion of the patient contact perimeter. The adhesive seal may comprise one or more layers. Each layer may include one or more cover members, each of which may include at least one removable tab; and at least one perforation. Each layer may further include a dual-sided form carrier with adhesive material on one or both sides.

18 Claims, 6 Drawing Sheets

(56) References Cited

U.S. PATENT DOCUMENTS

| | | | |
|---|---|---|---|
| 2007/0215161 A1* | 9/2007 | Frater | A61M 16/065 128/206.24 |
| 2014/0360502 A1* | 12/2014 | Kushida | A61M 16/0694 128/206.25 |
| 2015/0027447 A1* | 1/2015 | Leevan | A61M 16/0605 156/196 |
| 2020/0306483 A1* | 10/2020 | Chodkowski | A61M 16/0605 |
| 2020/0306484 A1* | 10/2020 | Chodkowski | A61M 16/0688 |
| 2021/0289853 A1* | 9/2021 | Bowen | A41D 13/1176 |
| 2022/0218931 A1* | 7/2022 | Hara | A61M 16/0611 |

* cited by examiner

POSITIVE PRESSURE VENTILATION APPARATUS AND POSITIVE PRESSURE MASK

FIELD OF THE TECHNOLOGY

The present disclosure relates generally to apparatuses for non-invasive ventilation of a patient requiring ventilatory care, and more specifically to an enhanced positive pressure mask which is configured to provide non-invasive ventilation without gas leak from the positive pressure mask when the patient moves their head. In particular, this disclosure relates to a positive pressure mask which can be adhered to the patient's face, as well as having a soft or flexible concertinaed portion which accommodates movement of the patient's head without introducing gas leaks.

INTRODUCTION

Medical professionals caring for patients with respiratory infections, particularly for highly infectious diseases such as the novel coronavirus disease 2019 (COVID-19), are at high risk of contracting the infection.

Aerosol-generating procedures, such as non-invasive ventilation, are of particularly high risk due to mask leaks, typically from around the edge of the mask where the mask meets the face.

Non-invasive ventilation units with an exhalation filter could be used to support acute pulmonary infectious disease patients with respiratory failure. However, the high incidence of mask leakage may result in incomplete filtration, as per Antonio M. Esquinas, S. Egbert Pravinkumar. Noninvasive mechanical ventilation in high-risk pulmonary infections: a clinical review on behalf of the International NIV Network European Respiratory Review 2014 23: 427-438.

This was demonstrated during the Severe Acute Respiratory Syndrome (SARS) pandemic of November 2002, in which non-invasive ventilation created aerosol generation to allow airborne transmission of the virus. There are many case reports of considerable SARS transmission risk with the use of non-invasive ventilators to many patients over extended distances, as per Li Y, Huang X, Yu I T, Wong T W, Qian H. Role of air distribution in SARS transmission during the largest nosocomial outbreak in Hong Kong. Indoor Air 2005; 15: 83-95. Poorly positioned masks result in leaked gas at the masks, causing aerosol dispersion and increasing the risk to medical professionals.

Due to the significant risk of infection to the medical practitioner providing care for a patient with a highly contagious respiratory disease such as COVID-19, mechanical ventilation is the primary mechanism for care, despite the risk to the patient of an invasive intervention.

Typically, to prevent cross-infection, practitioners progressively tighten mask straps to reduce the risk of mask leaks. However, if this method is employed for an extended period of time, it significantly increases the incidence of mask-related facial skin breakdown, as per Wellington P. Yamaguti, Eliana V. Moderno, Sandra Y. Yamashita, et al. Treatment-Related risk factors for the development of skin breakdown in subjects with acute respiratory failure undergoing noninvasive ventilation or Continuous Positive Airway Pressure ("CPAP"). Respiratory Care 2014 59(10), 1530. Progressively increasing strap tension to eliminate gas leakage is a primary cause of facial skin pressure ulcers. Jaber S. Alqahtani, Mohammed D. AlAhmari, Evidence based synthesis for prevention of noninvasive ventilation related facial pressure ulcers. Saudi Med J. 39(5), 443-552.

The novel application of adhesive at or near the mask perimeter to form a seal will allow practitioners to avoid progressive tightening of mask straps while also improving gas sealing. Furthermore, the use of adhesive instead of, or in addition to, straps is more resistant to patient movements and other displacements which would otherwise result in leakage and aerosol escape from the mask.

The application of an interchangeable, modular, multilayered adhesive seal at the mask perimeter will furthermore allow this single patient use device to be reused on the same patient.

SUMMARY

An aspect of the present disclosure may include a positive pressure ventilation apparatus. The positive pressure ventilation apparatus may include a positive pressure mask; a positive pressure source coupled to the positive pressure mask; and an exhalation filter positioned on a gas flow path interconnecting the positive-pressure source and positive pressure mask. The positive pressure mask may include a mask body configured to cover a patient's mouth and nostrils. The mask body may have a patient-contact perimeter and include a flexible concertinaed portion of uniform flexion continuously around the mask body. The flexible concertinaed portion may include a plurality of ridges. The plurality of ridges may be configured to be stacked perpendicular to the patient's face. The positive pressure mask may further include a gas inlet to the mask body configured to be connected to the positive-pressure source; and an adhesive seal positioned at the patient-contact perimeter. The adhesive seal may be positioned at the outermost portion of the patient contact perimeter. The adhesive seal may further comprise one or more layers. Each layer may include one or more cover members. Each cover member may include at least one removable tab; and at least one perforation. Each layer may further include a dual-sided form carrier 4 with adhesive material on one or both sides.

In an embodiment, the patient-contact perimeter comprises a cushioned portion. The cushioned portion may comprise a gel cushion In another embodiment, the mask body is at least in part light-transmissible.

In another embodiment, the adhesive seal is modular and interchangeable.

In yet another embodiment, the positive pressure ventilation apparatus may further comprise a strap for engaging with the patient's head to hold the positive pressure mask in position.

In a further embodiment, the gas inlet comprises an elbow swivel assembly.

In an embodiment, there is a uniform distance between the flexible concertinaed portion and the patient-contact perimeter around at least a majority of the mask body.

An aspect of the present disclosure may comprise a mask body configured to cover a patient's mouth and nostril. The mask body may have a patient-contact perimeter. The mask body may comprise an, at least in part, flexible portion of uniform flexion continuously around the mask body. The flexible concertinaed portion may comprise a plurality of ridges at or adjacent to the patient-contact perimeter to accommodate movement of the patient's face during use. The plurality of ridges may be configured to be stacked perpendicular to the patient's face, such that the plurality of ridges are configured to move away from and toward the patient's face. The positive pressure mask may further include a gas inlet to the mask body configured to be connected to a positive-pressure source; and an adhesive seal positioned at the patient-contact perimeter to secure the mask body to the patient's face. The adhesive may be positioned at an outermost portion of the patient contact perimeter. The adhesive seal may further comprise one or more layers. Each layer may comprise one or more cover members, each cover member may comprise at least one removable tab; and at least one perforation. Each layer may further include a dual-sided form carrier 4 with adhesive material on one or both sides.

In an embodiment, the patient-contact perimeter comprises a cushioned portion. The cushioned portion may comprise a gel cushion.

In another embodiment, the adhesive seal is modular and interchangeable.

In yet another embodiment, the gas inlet comprises an elbow swivel assembly.

An aspect of the present disclosure may comprise a mask body configured to cover a patient's mouth and nostril. The mask body may have a patient-contact perimeter. The mask body may comprise a flexible concertinaed portion at or adjacent to the patient-contact perimeter to accommodate movement of the patient's face during use. The flexible concertinaed portion may comprise a plurality of ridges configured to be stacked perpendicular to the patient's face, such that the plurality of ridges are configured to move away from and toward the patient's face. The positive pressure mask may further include a gas inlet to the mask body configured to be connected to a positive-pressure source; and an adhesive seal positioned at the patient-contact perimeter to secure the mask body to the patient's face. The adhesive seal may be positioned at an outermost portion of the patient contact perimeter The adhesive seal may further comprise one or more layers. Each layer may comprise one or more cover members and a dual-sided form carrier 4 with adhesive material on one or both sides. Each cover member may comprise at least one removable tab, and at least one perforation.

In an embodiment, the mask body is formed from a flexible plastics material.

In another embodiment, the adhesive seal is modular and interchangeable.

In yet another embodiment, the flexible concertinaed portion is continuous around the mask body to permit uniform flexion.

In a further embodiment, there is a uniform distance between the flexible concertinaed portion and the patient-contact perimeter around at least a majority of the mask body.

Additional aspects related to this disclosure are set forth, in part, in the description which follows, and, in part, will be obvious from the description, or may be learned by practice of this disclosure.

It is to be understood that both the forgoing and the following descriptions are exemplary and explanatory only and are not intended to limit the claimed disclosure or application thereof in any manner whatsoever.

BRIEF DESCRIPTION OF THE DRAWINGS

The incorporated drawings, which are incorporated in and constitute a part of this specification, exemplify the aspects of the present disclosure and, together with the description, explain and illustrate principles of this disclosure.

DETAILED DESCRIPTION

In the following detailed description, reference will be made to the accompanying drawing(s), in which identical functional elements are designated with like numerals. The aforementioned accompanying drawings show, by way of illustration, and not by way of limitation, specific aspects, and implementations consistent with principles of this disclosure. These implementations are described in sufficient detail to enable those skilled in the art to practice the disclosure and it is to be understood that other implementations may be utilized and that structural changes and/or substitutions of various elements may be made without departing from the scope and spirit of this disclosure. The following detailed description is, therefore, not to be construed in a limited sense.

Figure 1:
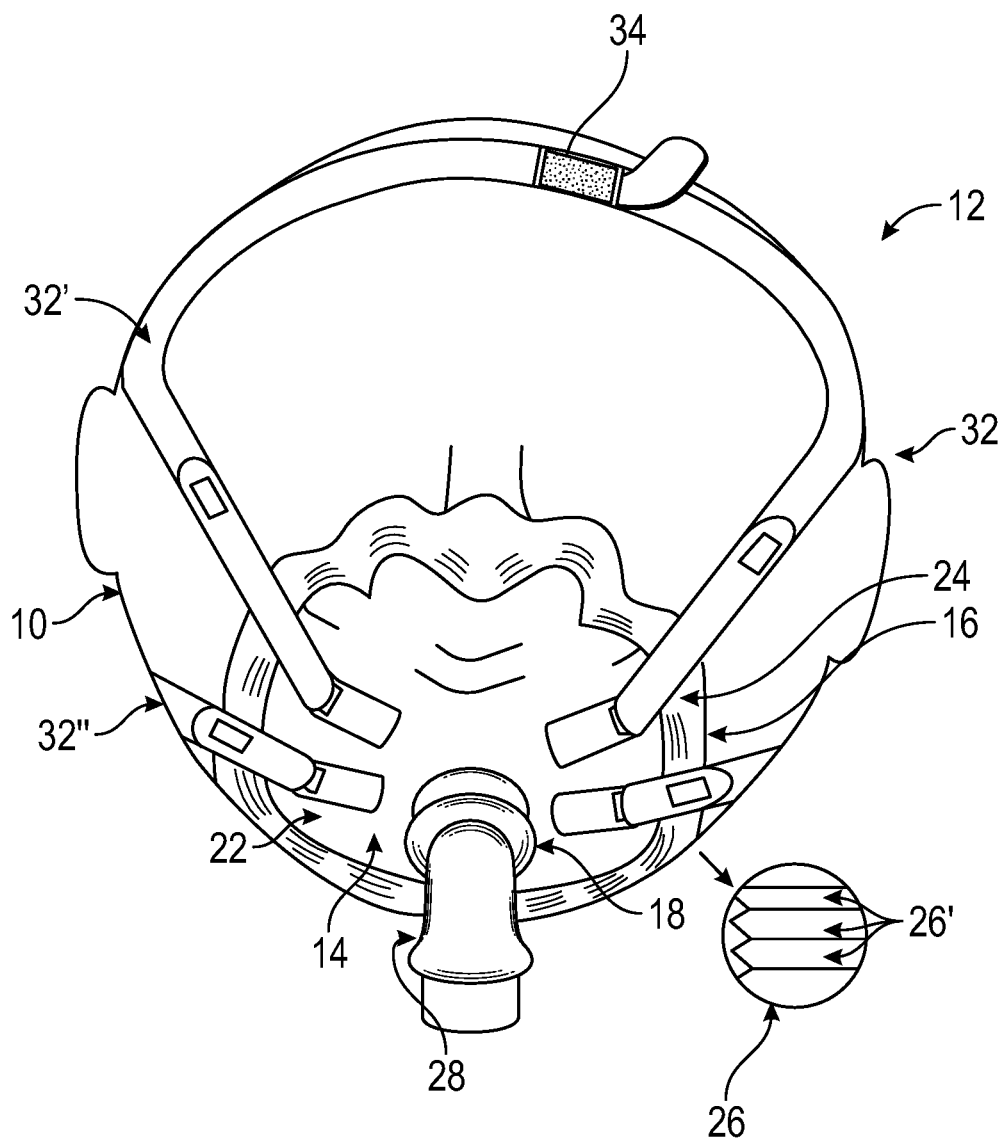
FIG. 1 shows a patient wearing an indicative embodiment of a positive pressure mask in accordance with one aspect of the invention, from the front, with an inset showing the concertinaed portion structure of the mask body and the distal flange 46.

Turning to FIG. 1, there is illustrated a patient 10 wearing a positive pressure mask 12 in accordance with the present disclosure.

The positive pressure mask 12 may include a mask body 14 which is receivable over the patient's mouth and nose, so as to cover the mouth and nostrils. The mask body 14 may be formed from a flexible material, such as silicone, biocompatible thermoplastic polyurethane, or any gel-like materials such that it may be capable of conforming to the contours of the patient's face at or adjacent to a patient-contact perimeter 16 thereof. However, the mask body 14 may be contoured and dimensioned so as to fit around a predetermined dimension and shape of a patient's face. In such a case, a more rigid mask body 14 material may be used.

Figure 2:
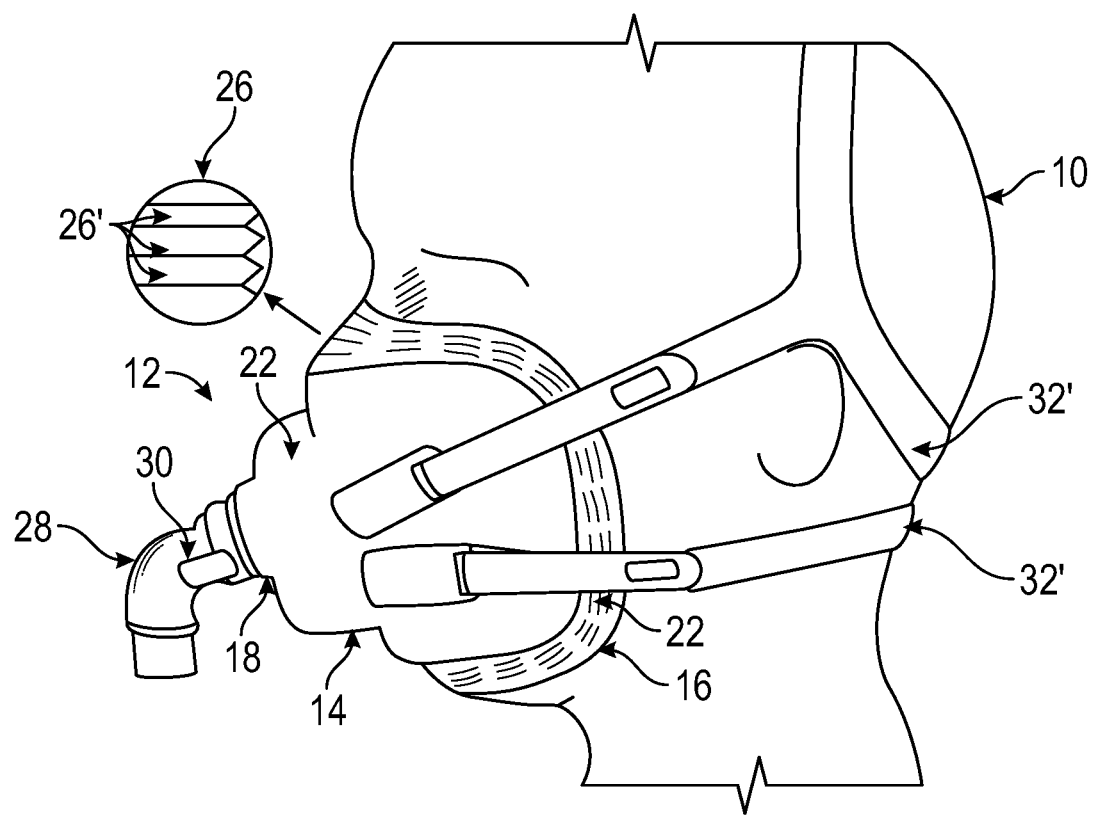
FIG. 2 shows the patient wearing the positive pressure mask of FIG. 1, from the side.

To cover the user's respiratory access, that is, the nostrils and mouth, the mask body 14 may be configured to overlie the nostrils and the cheeks. The patient-contact perimeter 16 therefore may form the points of contact with the patient 10, as best illustrated in FIG. 2.

The mask body 14, when positioned over the patient's face, may form a ventilation chamber which may be pressurized to urge air or oxygen from a gas inlet 18 of the positive pressure mask 12 into the patient's lungs.

Figure 3:
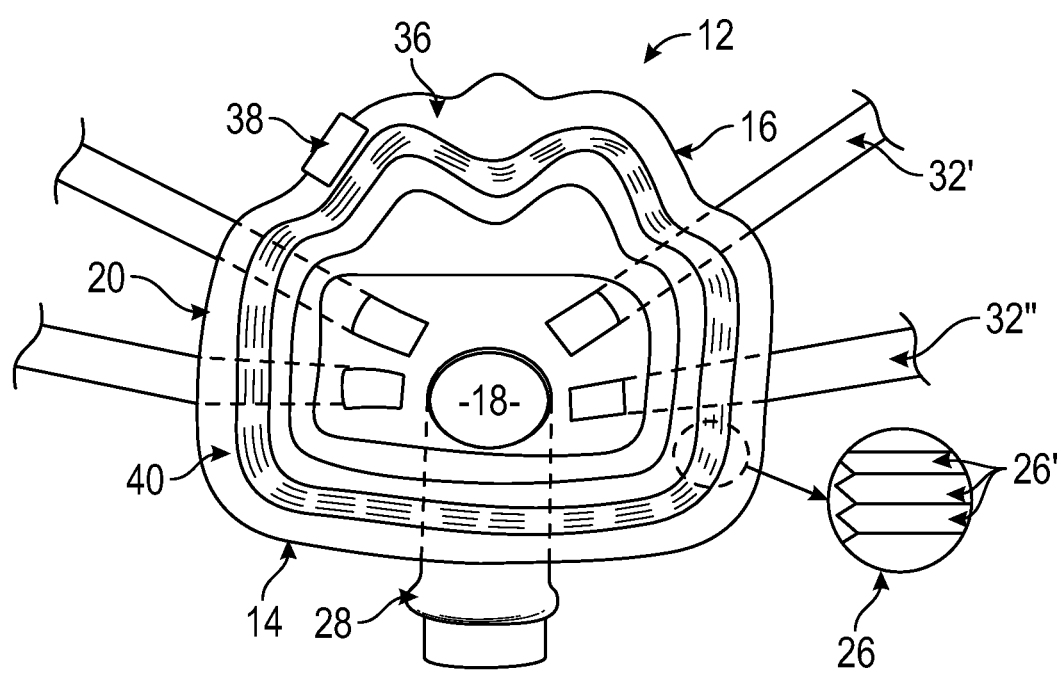
FIG. 3 shows the positive pressure mask of FIG. 1 from the patient-facing direction, with an inset showing the concertinaed portion structure of the mask body.
Figure 5:
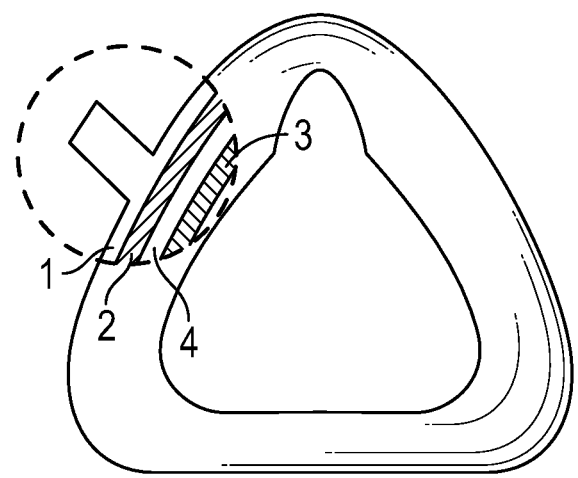
FIG. 5 shows an indicative embodiment of an adhesive seal.
Figure 6:
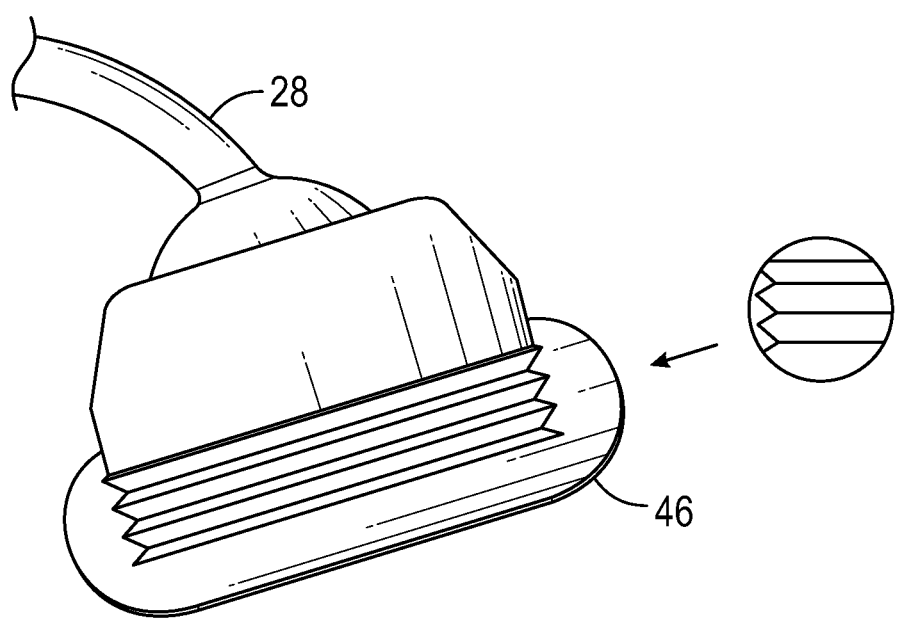
FIG. 6 illustrates a portion of the positive pressure mask, showing an alternate view the distal flange 46 portion.

To ensure that the ventilation chamber is sealed to the atmosphere, and in order to inhibit release of aerosols and therefore potential contagions for a medical practitioner, the positive pressure mask 12 advantageously may include an adhesive seal 20, best seen in FIGS. 3 and 5, positioned at the patient-contact perimeter 16 to secure the mask body 14 to the patient's face. The adhesive seal 20 may prevent or reduce gas leakage from the ventilation chamber.

The mask body 14 may include two separate body portions. Firstly, there may be a main body portion 22 which forms the bulk of the ventilation chamber, and which may be formed from a rigid or flexible material.

The main body portion 22 may have a small projecting profile beyond the patient's mouth and/or nose, in order to minimize wasted volume in the ventilation chamber which could otherwise lead to carbon dioxide rebreathing for the patient. In an embodiment, the main body portion 22 is formed from, or includes at least in part, a light-transmissible material, such as a transparent plastic material. In another embodiment, the light-transmissible material is fully see-through, allowing the medical practitioner to visually inspect the patient through the positive pressure mask 12 without needing to remove the positive pressure mask 12. In yet another embodiment, the main body portion 22 may include a lightweight, flexible body made from silicone elastomer or other similar material.

Secondly, the mask body 14 may include a ridged body portion 24. This ridged body portion 24 may include a distal flange 46 to support the adhesive seal 20. The mask body 14 may furthermore be positioned at or adjacent to the patient-contact perimeter 16 to permit deformation of the mask body 14 during movement of the patient 10. This ridged body portion 24 may include a soft or flexible concertinaed portion 26, which allows for compressive or bellows-like motion similar to that of an accordion.

This structure may be best seen in the inset portions of FIGS. 1 and 2. The flexible concertinaed portion 26 may include at least one concertina ridge 26', preferably at least two said concertina ridges 26', and even at least three concertina ridges 26'. This may achieve deformable flexibility at or adjacent to the patient-contact perimeter 16. The positive pressure mask 12 having such a flexible concertinaed portion 26 may be able to accommodate movements of the patient's head within the flexion of the concertina ridges 26', despite the lag or tension experienced by the mask body 14 from the gas inlet 18.

To further limit the pull on the mask body 14 at the gas inlet 18, the gas inlet 18 may include a movable connector, such as an elbow swivel assembly 28. This may permit rotation around the mask body 14 which may counteract the deformation of the flexible concertinaed portion 26 without increasing the forces thereon. The right-angled or near-right-angled elbow joint of the elbow swivel assembly 28 may be particularly appropriate for a prone patient 10. The elbow swivel assembly 28 may be provided so as to be integrally formed with the mask body 14, or may be a removable or releasably engageable component of the positive pressure mask 12, thereby allowing for a more modular construction to be achieved. A releasable connector 30 is illustrated in FIG. 2 in the form of a quick-release snap-fit connector. However, alternative connectors may be provided, such as detent fit or screw-threaded engagement, and alternative connection mechanisms will be apparent to the skilled person.

To improve the positioning of the positive pressure mask 12 on the patient 10, as well to limit the propensity for de-adhesion of the adhesive seal 20 over time, a strap 32 for engaging with the patient's head may be provided. The strap 32 may be adjustable.

An upper strap 32' may be provided, which may engage from an upper portion of the mask body 14, which connects to the upper portion of the patient's head, typically above the ears. A bifurcated head strap 32 may be provided to secure to both the upper and lower occipital areas of the patient's head. A lower strap 32" may also be provided, which may engage from a lower portion of the mask body 14 below the level of the ears, and around an upper portion of the patient's neck.

The strap 32 may be composed of silicone. In another embodiment, the strap 32 may be made of synthetic neoprene or nylon or elastane fabric. In yet another embodiment, the strap 32 may include hook-and-loop fasteners, such as VELCRO™, to secure the mask in place. Alternatively, latch, buckle, or tied fasteners may be used.

An adjustable connector 34 may be provided so that the strap 32 can be used with patients of different sizes. Here, a hook-and-loop type fastener may be provided, but alternative latch, buckle, or tied fasteners may readily be implemented by the person skilled in the art.

The upper strap 32' and lower strap 32" may be connected to the mask body 14 via connectors on the front of the mask body 14, preferably on the main body portion 22 so as to avoid interfering with the flexible concertinaed portion 26.

FIG. 3 shows the inside of the positive pressure mask 12. In a pre-use condition, the adhesive seal 20 may be protected by a cover member 36 to prevent drying out of the adhesive. This cover member 36 may be releasably engageable with the adhesive seal 20, for example, by the use of a release tab 38 at or adjacent to the patient-contact perimeter 16. This may allow the adhesive seal 20 to only become activated when required. Alternative release mechanisms may be considered instead of a tab, such as a perforation, or overhang of the material of the cover member 36 or protruded engageable loop.

The gas inlet 18 may be positioned so as to be at or adjacent to a mouth position of the patient 10, so as to reduce the dead space in the ventilation chamber.

To improve the comfort of the positive pressure mask 12 for the patient 10, a cushioned portion may be provided. The cushioned portion may comprise gel, such as in an embodiment with a silica gel cushion 40. In another embodiment, the cushioned portion may comprise a silicone elastomer. In yet another embodiment, the cushioned portion may comprise memory foam.

In an embodiment, the cushioned portion is adjacent to the adhesive seal 20. In yet another embodiment, the cushioned portion further comprises the adhesive seal 20 such that the cushioned portion may be directly adhered to the patient 10. Given that the adhesive seal 20 may be positioned on the patient 10 for a long period of time, the cushioned portion will improve comfort for the patient 10.

In an embodiment of the mask body 14 there is uniform flexion around the flexible concertinaed portion 26, since this will permit movement in all directions. In another embodiment, the flexible concertinaed portion 26 further comprises a distal flange 46 to position and secure the modular, interchangeable adhesive seal 20. In said embodiment the distal flange 46 has the same range of motion as the flexible concertinaed portion 26.

The flexible concertinaed portion 26 may be continuous around the mask body 14 to permit said uniform flexion. A uniform distance between the flexible concertinaed portion 26 and the patient-contact perimeter 16 and/or adhesive seal 20 at least a majority of the mask body 14 may also assist in this regard. In FIG. 3, there may be a minor change in the distance between the patient-contact perimeter 16 and the flexible concertinaed portion 26 at the bridge of the nose, but this will not have a significant effect on the flexible capabilities of the positive pressure mask 12 since there will be minimal movement at the nose.

Figure 4:
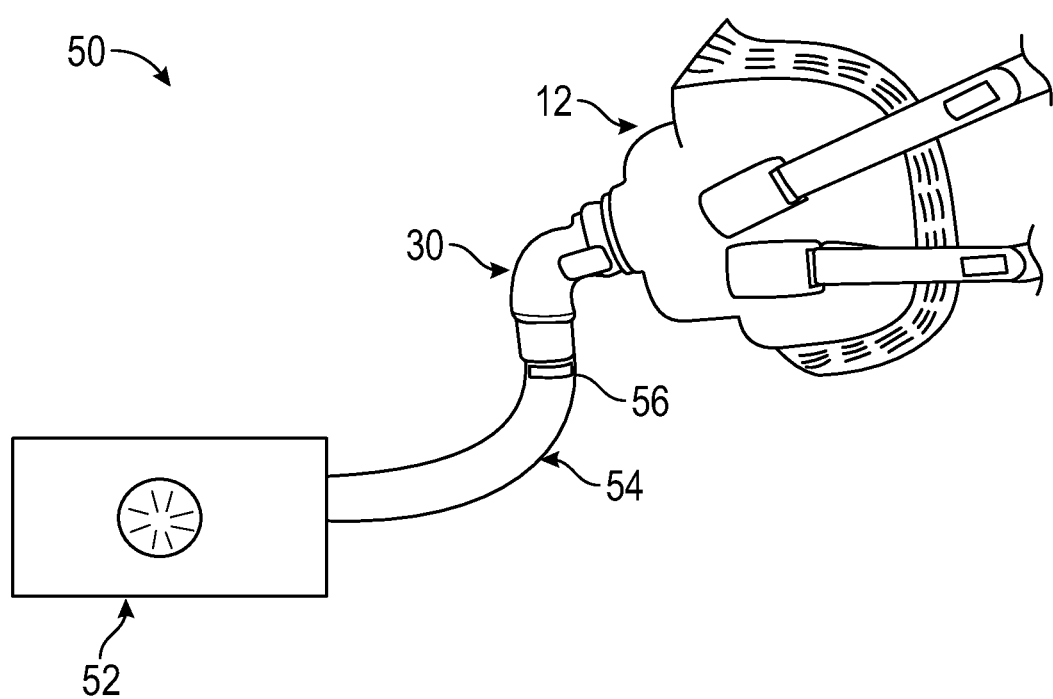
FIG. 4 shows a positive pressure ventilation apparatus in accordance with the invention.

FIG. 4 shows a positive pressure ventilation apparatus, referenced globally at 50, utilizing the positive pressure mask 12 as previously described.

The positive pressure mask 12 may be connected to a positive-pressure source 52, such as a peristaltic pump used as a ventilator, which may enable pressurized gas flow along a gas flow path between the pump and the positive pressure mask 12. The gas flow path may be formed by the provision of a connector conduit 54 extending from the positive-pressure source 52 and the positive pressure mask 12, and any appropriate type of gas-tight connector may be used here which is suitable for medical-grade use. In an embodiment, the gas-tight connector may further comprise a single limb circuit, such that the exhalation is accommodated via a gas circuit exhalation port with an attached gas exhalation filter. In another embodiment, the gas-tight connector further comprises a double limb circuit, such that the exhalation filter 56 is attached directly between the elbow swivel assembly 28 connector and the gas circuit.

An exhalation filter 56 may advantageously be positioned on a gas flow path, which may filter out contagions from the patient's exhaled breath. The exhalation filter 56 may be positioned as close to the positive pressure mask 12 as is feasible, and is illustrated in FIG. 4 as being directly subsequent to the elbow swivel assembly 28. It will be apparent that the exhalation filter 56 could be provided further along the gas flow path, for example, closer to the positive-pressure source 52, or could indeed be integrally formed with the positive pressure mask 12.

The positive pressure ventilation apparatus 50 may provide a complete system for non-invasively ventilating a patient 10 in need of ventilatory care. The positive pressure ventilation apparatus 50 may be provided as a kit of parts, or may be provided as a complete set of components.

To use the positive pressure ventilation apparatus 50, the apparatus may be assembled, that is, the positive pressure mask 12 may be provided, and the positive-pressure source 52 coupled to the positive pressure mask 12, preferably with the exhalation filter 56 positioned on a gas flow path interconnecting the positive-pressure source 52 and positive pressure mask 12. In another embodiment, the exhalation filter 56 is incorporated directly into the body of the positive pressure mask 12.

The positive pressure mask 12 may then be engaged over the patient's face and adhered to the patient 10 via the adhesive seal 20 at or adjacent to the patient-contact perimeter 16. In an embodiment, the adhesive seal 20 comprises one or more layers of form-carried adhesive material. The adhesive seal 20 may be coupled to the mask body 14 via a distal flange 46 on the flexible concertinaed portion 26. The adhesive seal 20 at the patient-contact perimeter 16 may prevent gas leakage during flexion of the flexible concertinaed portion 26. The positive-pressure source 52 may then be activated to ventilate the patient 10.

While the positive pressure mask 12 is herein described as having an adhesive seal 20 in combination with a flexible concertinaed portion 26, it will be apparent to the skilled person that an adhesive seal 20 could be provided with existing positive pressure masks, or indeed with other types of respiratory masks, to achieve improved sealing and therefore reduced cross-infection possibilities. A respiratory mask, and in particular, a positive pressure mask 12, having an adhesive seal 20 at or adjacent to a patient-contact perimeter 16 of the mask body 14, may therefore be considered to be within the scope of the present invention. This arrangement may be particularly effective in combination with a cushioned portion at or adjacent to the adhesive seal 20, the adhesive seal 20 may be coupled to the distal flange 46 of the flexible concertinaed portion 26 of the mask body 14, the adhesive seal 20 may further comprise multiple layers of form-carried adhesive material, and the adhesive seal 20 may be furthermore modular and interchangeable.

Similarly, a positive pressure mask 12 having a flexible concertinaed portion 26 at or adjacent to the patient-contact perimeter 16, could be provided in the absence of an adhesive seal 20. In particular, the head straps of the positive pressure mask 12 could be provided to create a sufficient seal without the need for adhesive on the patient's face. This may be particularly effective if the patient-contact perimeter 16 is formed from a deformable or flexible material so as to tightly contour to the patient's face when the positive pressure mask 12 is applied.

While a flexible concertinaed portion 26 is described, it will be apparent that the ridged structure may be akin to a bellows, and could be described as such. Furthermore, while a concertina shape is disclosed, alternative constructions may be considered. For example, the mask body 14 could comprise the main body portion 22, formed of a comparatively rigid or hard material, while the flexible portion at/or adjacent to the patient-contact perimeter 16 may be provided as a softer or more flexible material, without necessarily needing to provide the concertina structure proposed above. Silicone, biocompatible thermoplastic polyurethane, and gel-like materials may also be used at/or adjacent to the patient-contact perimeter 16.

As noted previously, any of the advantageous features of the present invention could be applied to respiratory masks other than positive pressure masks, and such mask arrangements are not excluded from the scope of the present invention.

A flexible transparent or translucent material may be preferred for the mask body 14. In another embodiment, the mask body 14 may comprise silicone or biocompatible thermoplastic polyurethane. However, it will be apparent that other materials could be used without any corresponding deterioration in the gas-tightness, without compromising the function of the positive pressure mask 12.

It is therefore possible to provide positive pressure equipment for ventilating a patient in a non-invasive manner while significantly reducing the risk of transmission of contagions to, in particular, medical practitioners. The positive-pressure mask may use an adhesive seal 20 to improve the sealing capabilities of the mask to the patient's face, while the flexible concertinaed portion 26 of the mask may allow for limited movement of the mask, particularly under the weight of the connectors to the positive-pressure source 52, without creating gas leakage. This may provide improved patient ventilation capabilities without the need for an invasive solution.

As shown in FIG. 5, the distal flange 46 of the flexible concertinaed portion 26 may be used to couple the adhesive seal 20 to the patient-contact perimeter 16 of the mask body 14, the adhesive seal 20 may further comprise one or more layers of form-carried adhesive material. In an embodiment, the adhesive seal 20 is attached to the distal flange 46 via acrylate adhesive or other synthetic rubber adhesive.

In an embodiment, the adhesive seal 20 comprises one or more layers of form-carried adhesive material. In said embodiment, each layer of form-carried adhesive material comprises a form carrier 4, with one or more sides of the form carrier 4 having adhesive material. The form carrier 4 may be made from woven cloth, non-woven polyesters, or polymeric film. In an embodiment, the adhesive layer comprises soft silicone gel adhesive 3 at the patient-contact perimeter 16 to adhere the form carrier 4 to the facial skin. In another embodiment, both sides of the form carrier 4 have adhesive material.

The adhesive seal 20 may further comprise one or more cover members 36 to protect the form-carried adhesive material 2 in pre-use condition. The cover member 1 may further comprise multiple release tabs, perforations, or other means for removing the cover member 1 from the adhesive layer. The cover member 1 may comprise paper material, woven cloth, non-woven polyesters, or polymeric film In an embodiment of the adhesive seal 20, at least two form-carried adhesive materials are arranged in a layered formation. When the first form-carried adhesive material is no longer performing as desired, and the user wants to gain access to the second form-carried adhesive material, the user may remove the first form-carried adhesive material to reveal the second form-carried adhesive material. A cover member 36 may separate the first form-carried adhesive material from the second form-carried adhesive material 2.

In a preferred embodiment, the adhesive seal 20 is modular and interchangeable. In the pre-use condition of said embodiment, a first cover member 1 will couple with the side of the form-carried adhesive material 2 that will be joined to the distal flange 46 of the flexible concertinaed portion 26, and a second cover member 36 will couple with the side of the first form-carried adhesive material 2 that will adhere to the patient 10.

When the last available form-carried adhesive material 2 is no longer performing as desired, the user may remove said form-carried adhesive material from the distal flange 46 of the flexible concertinaed portion 26 and may replace it with another adhesive seal 20 by removing the first cover member of the adhesive seal 20 and adhering the form-carried adhesive material to the distal flange 46 of the flexible concertinaed portion 26.

In another embodiment, the adhesive seal 20 may be attached to the cushioned portion of the mask body 14.

In yet another embodiment, the cushioned portion comprises adhesive material at the patient-contact perimeter 16 such that the mask cushion may be adhered directly to the patient 10. In an embodiment, the adhesive material comprises soft silicone gel adhesive 3 at the patient-contact perimeter 16.

The words 'comprises/comprising' and the words 'having/including' when used herein with reference to the present invention are used to specify the presence of stated features, integers, steps or components, but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The embodiments described above are provided by way of examples only, and various other modifications will be apparent to persons skilled in the field without departing from the scope of the invention as defined herein.

What is claimed is:

1. A positive pressure ventilation apparatus, comprising:
a positive pressure mask;
a positive-pressure source coupled to the positive pressure mask;
an exhalation filter positioned on a gas flow path interconnecting the positive-pressure source and positive pressure mask,
the positive pressure mask comprising:
a mask body configured to cover a patient's mouth and nostrils, the mask body having a patient-contact perimeter, the mask body comprising a flexible concertinaed portion of uniform flexion continuously around the mask body, the flexible concertinaed portion comprising a plurality of ridges, at or adjacent to the patient-contact perimeter to accommodate movement of the patient's face during use, the plurality of ridges configured to be stacked perpendicular to the patient's face, such that the plurality of ridges are configured to move away from and toward the patient's face;
a gas inlet to the mask body configured to be connected to the positive-pressure source; and
an adhesive seal positioned at the outermost portion of the patient contact perimeter comprising:
two or more layers of form-carried adhesive material;
arranged in a layered formation separable by a removable tab;
wherein each layer is separated by a cover member.

2. The positive pressure ventilation apparatus as claimed in claim 1, wherein the patient-contact perimeter comprises a cushioned portion.

3. The positive pressure ventilation apparatus as claimed in claim 2, wherein the cushioned portion comprises a gel cushion.

4. The positive pressure ventilation apparatus as claimed in claim 1, wherein the mask body is at least in part light-transmissible.

5. The positive pressure ventilation apparatus as claimed in claim 1, wherein the adhesive seal is modular and interchangeable.

6. The positive pressure ventilation apparatus as claimed in claim 1, further comprising a strap for engaging with a patient's head to hold the positive pressure mask in position.

7. The positive pressure ventilation apparatus as claimed in claim 1, wherein the gas inlet comprises an elbow swivel assembly.

8. The positive pressure ventilation apparatus as claimed in claim 1, wherein there is a uniform distance between the flexible concertinaed portion and the patient-contact perimeter around at least a majority of the mask body.

9. A positive pressure mask, comprising:
a mask body configured to cover a patient's mouth and nostrils, the mask body having a patient-contact perimeter, the mask body comprising an at least in part flexible portion of uniform flexion continuously around the mask body, a flexible concertinaed portion comprising a plurality of ridges, at or adjacent to the patient-contact perimeter to accommodate movement of the patient's face during use, the plurality of ridges configured to be stacked perpendicular to the patient's face, such that the plurality of ridges are configured to move away from and toward the patient's face;
a gas inlet to the mask body configured to be connected to a positive-pressure source; and
an adhesive seal positioned at the outermost portion of the patient contact perimeter comprising:
two or more layers of form-carried adhesive material; arranged in a layered formation separable by a removable tab;
wherein each layer is separated by a cover member.

10. The positive pressure mask as claimed in claim 9, wherein the patient-contact perimeter comprises a cushioned portion.

11. The positive pressure mask as claimed in claim 9, further including a cushioned portion comprising a gel cushion.

12. The positive pressure mask as claimed in claim 9, wherein the adhesive seal is modular and interchangeable.

13. The positive pressure mask as claimed in claim 9, wherein the gas inlet comprises an elbow swivel assembly.

14. A positive pressure mask, comprising:
- a mask body configured to cover a patient's mouth and nostrils, the mask body having a patient-contact perimeter,
- the mask body comprising a flexible concertinaed portion at or adjacent to the patient-contact perimeter to accommodate movement of the patient's face during use, the flexible concertinaed portion comprising a plurality of ridges, the plurality of ridges configured to be stacked perpendicular to the patient's face, such that the plurality of ridges are configured to move away from and toward the patient's face;
- a gas inlet to the mask body configured to be connected to a positive-pressure source; and
- an adhesive seal positioned at the outermost portion of the patient contact perimeter comprising:
  - two or more layers of form-carried adhesive material; arranged in a layered formation separable by a removable tab;
  - wherein each layer is separated by a cover member.

15. The positive pressure mask as claimed in claim 14, wherein the mask body is formed from a flexible plastics material.

16. The positive pressure mask as claimed in claim 14, wherein the adhesive seal is modular and interchangeable.

17. The positive pressure mask as claimed in claim 14, wherein the flexible concertinaed portion is continuous around the mask body to permit uniform flexion.

18. The positive pressure mask as claimed in claim 14, wherein there is a uniform distance between the flexible concertinaed portion and the patient-contact perimeter around at least a majority of the mask body.

* * * * *